(12) United States Patent
Hasegawa et al.

(10) Patent No.: US 9,345,396 B2
(45) Date of Patent: May 24, 2016

(54) SCANNING ENDOSCOPE SYSTEM

(71) Applicant: OLYMPUS MEDICAL SYSTEMS CORP., Tokyo (JP)

(72) Inventors: Jun Hasegawa, Hino (JP); Katsumi Hirakawa, Sagamihara (JP); Yuji Sakai, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/162,164

(22) Filed: Jan. 23, 2014

(65) Prior Publication Data
US 2014/0184768 A1    Jul. 3, 2014

Related U.S. Application Data

(63) Continuation of application No. PCT/JP2013/063023, filed on May 9, 2013.

(30) Foreign Application Priority Data

Sep. 19, 2012  (JP) .................. 2012-206102

(51) Int. Cl.
*A61B 1/04*      (2006.01)
*A61B 1/06*      (2006.01)
(Continued)

(52) U.S. Cl.
CPC ........... *A61B 1/0661* (2013.01); *A61B 1/00172* (2013.01); *A61B 1/045* (2013.01);
(Continued)

(58) Field of Classification Search
CPC ............... G02B 27/025; G02B 27/027; A61B 1/00193; A61B 1/00163; A61B 1/00165; A61B 1/00167; A61B 1/00172; A61B 1/045

USPC .......................................................... 348/68
See application file for complete search history.

(56) References Cited

U.S. PATENT DOCUMENTS

2010/0121146 A1    5/2010  Sugimoto
2010/0137684 A1*   6/2010  Shibasaki et al. ............. 600/109

FOREIGN PATENT DOCUMENTS

JP      2010-063497       *   3/2010
JP      2010-063497  A       3/2010
(Continued)

OTHER PUBLICATIONS

Extended Supplementary European Search Report dated Dec. 14, 2015 from related European Application No. 13 84 0096.5.

*Primary Examiner* — Mehrdad Dastouri
*Assistant Examiner* — Kristin Dobbs
(74) *Attorney, Agent, or Firm* — Scully, Scott, Murphy & Presser, P.C.

(57) ABSTRACT

A scanning endoscope system has a light guide portion that guides an illuminating light, a drive portion capable of causing the light guide portion to swing so that an irradiation position of the illuminating light draws a locus corresponding to a predetermined scanning pattern, a light detecting portion that receives a return light of the illuminating light and outputs a signal, a control portion that drives the drive portion to perform scan so that the irradiation position of the illuminating light becomes a locus in a spiral shape, and an image generating portion that generates an image of an object based on a signal outputted from the light detecting portion in a predetermined timing, wherein the control portion further performs control for driving the drive portion so that the irradiation position of the illuminating light circles on a same circumference in the predetermined timing.

7 Claims, 10 Drawing Sheets

(51) Int. Cl.
  *H04N 9/47* (2006.01)
  *H04N 7/18* (2006.01)
  *G02B 23/26* (2006.01)
  *A61B 1/00* (2006.01)
  *G02B 23/24* (2006.01)
  *G02B 26/10* (2006.01)
  *A61B 1/045* (2006.01)

(52) U.S. Cl.
  CPC ............ *G02B23/2469* (2013.01); *G02B 23/26* (2013.01); *G02B 26/103* (2013.01); *A61B 1/04* (2013.01); *A61B 1/0669* (2013.01)

(56) References Cited

FOREIGN PATENT DOCUMENTS

| | | | |
|---|---|---|---|
| JP | 2010063497 A | * | 3/2010 |
| JP | 2010-131110 A | | 6/2010 |
| JP | 2010-131112 A | | 6/2010 |

* cited by examiner

SCANNING ENDOSCOPE SYSTEM

CROSS REFERENCE TO RELATED APPLICATION

This application is a continuation application of PCT/JP2013/063023 filed on May 9, 2013 and claims benefit of Japanese Application No. 2012-206102 filed in Japan on Sep. 19, 2012, the entire contents of which are incorporated herein by this reference.

BACKGROUND OF THE INVENTION

1. Field of the Invention

The present invention relates to a scanning endoscope system, and particularly relates to a scanning endoscope system that scans an object and acquires an image.

2. Description of the Related Art

In endoscopes in a medical field, in order to reduce the burdens on subjects, various techniques are proposed, which are for reducing the diameters of the insertion portions that are inserted into the body cavities of the subjects. As one example of the techniques as above, a scanning endoscope that does not have a solid image pickup device in the portion corresponding to the aforementioned insertion portion, and a system that is configured by including the scanning endoscope are known.

More specifically, the system including the aforementioned scanning endoscope is configured to scan an object in a scanning pattern that is set in advance by swinging the distal end portion of an illuminating fiber that guides an illuminating light that is emitted from the light source portion, receive the return light from the object with light receiving fibers disposed around the illuminating fiber, and generate an image of the object by using the signals obtained by separating the return light that is received by the light receiving fibers into respective color components.

As the system including the configuration as described above, the endoscope apparatus as disclosed in, for example, Japanese Patent Application Laid-Open Publication No. 2010-131112 has been conventionally known.

SUMMARY OF THE INVENTION

A scanning endoscope system of one aspect of the present invention has a light guide portion that guides an illuminating light emitted from a light source, a drive portion capable of causing the light guide portion to swing in such a manner that an irradiation position of the illuminating light that is irradiated to an object via the light guide portion draws a locus corresponding to a predetermined scanning pattern, a light detecting portion that is configured to receive a return light of the illuminating light that is irradiated to the object, generate a signal corresponding to intensity of the return light, and output the signal, a control portion that performs control for driving the drive portion to perform scanning so that the irradiation position of the illuminating light becomes a locus in a spiral shape, and an image generating portion that generates an image of the object based on a signal that is outputted from the light detecting portion in a predetermined timing of timings at which the drive portion is controlled, wherein the control portion further performs control for driving the drive portion so that the irradiation position of the illuminating light circles on a same circumference in the predetermined timing at which the image generating portion generates the image of the object.

DETAILED DESCRIPTION OF THE PREFERRED EMBODIMENT

Hereinafter, an embodiment of the present invention will be described with reference to the drawings.

Figure 1:
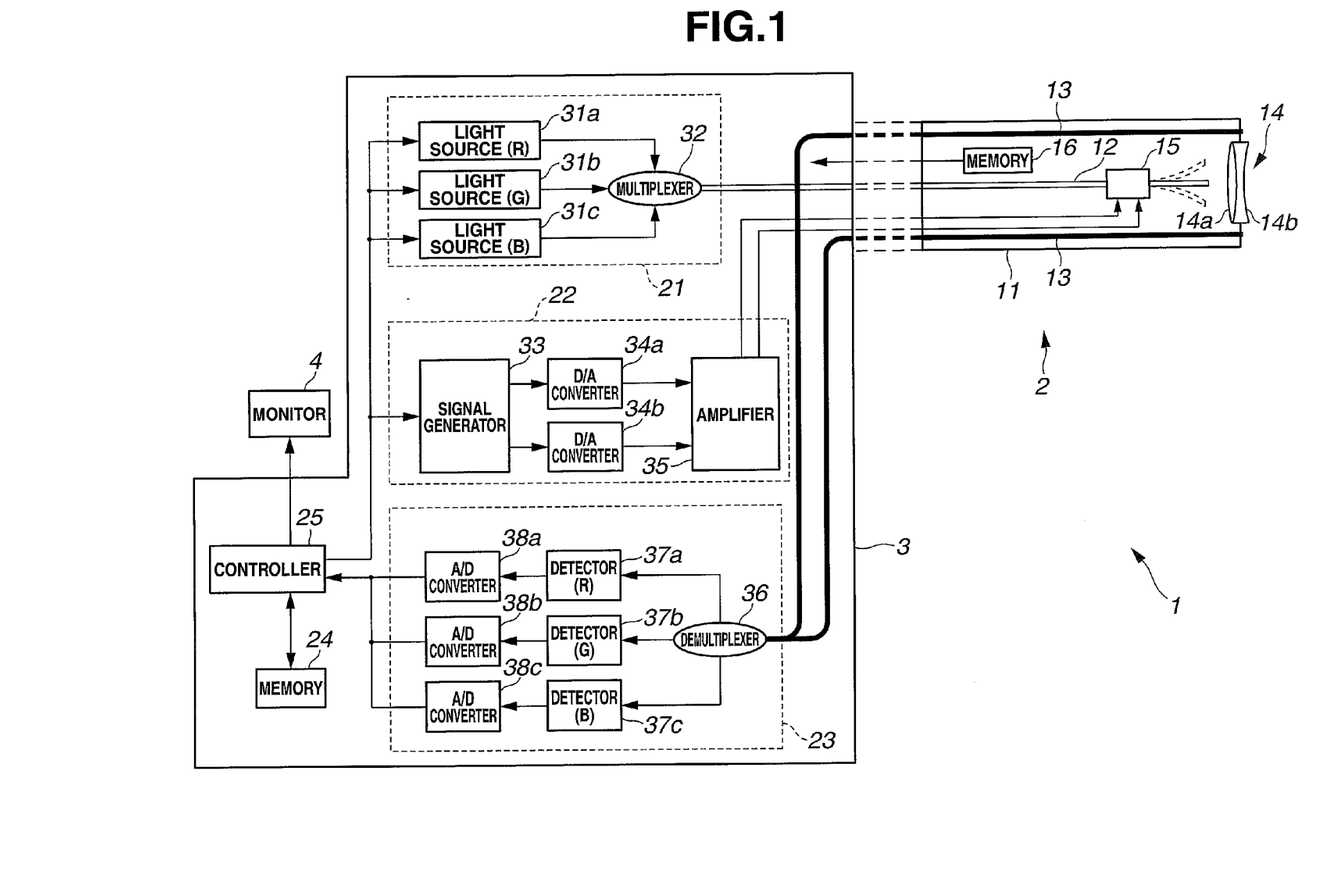
FIG. 1 is a diagram showing a configuration of an essential part of a scanning endoscope system according to an embodiment.

FIG. 1 to FIG. 13 relate to the embodiment of the present invention. FIG. 1 is a diagram showing an essential part of a scanning endoscope system according to the embodiment.

As shown in FIG. 1, for example, a scanning endoscope system 1 is configured by having a scanning endoscope 2 that is inserted into a body cavity of a subject, a main body apparatus 3 that is connected to the scanning endoscope 2, and a monitor 4 that is connected to the main body apparatus 3.

The scanning endoscope 2 is configured by having an insertion portion 11 that is formed by including an elongated shape and flexibility capable of being inserted into a body cavity of a subject. Note that at a proximal end portion of the insertion portion 11, a connector or the like not illustrated for detachably connecting the scanning endoscope 2 to the main body apparatus 3 is provided.

An illuminating fiber 12 including a function as a light guide portion that guides an illuminating light supplied from a light source unit 21 of the main body apparatus 3 to an objective optical system 14, and light receiving fibers 13 that receive a return light from an object and guide the return light to a detection unit 23 of the main body apparatus 3 are respectively inserted through a portion from the proximal end portion to a distal end portion inside the insertion portion 11.

An end portion including a light incident face of the illuminating fiber 12 is disposed in a multiplexer 32 provided inside the main body apparatus 3. Further, an end portion including a light exit face of the illuminating fiber 12 is disposed in a state in which the end portion is not fixed by a fixing member or the like, in a vicinity of a light incident face of a lens 14a provided at the distal end portion of the insertion portion 11.

An end portion including a light incident face of the light receiving fiber 13 is fixedly disposed in a surrounding of a light exit face of a lens 14b, in a distal end face of the distal end portion of the insertion portion 11. Further, an end portion including a light exit face of the light receiving fiber 13 is disposed in a demultiplexer 36 provided inside the main body apparatus 3.

The objective optical system 14 is configured by having the lens 14a on which the illuminating light from the illuminating fiber 12 is incident, and the lens 14b that emits the illuminating light passing through the lens 14a to an object.

An actuator 15 that drives based on a drive signal that is outputted from a driver unit 22 of the main body apparatus 3 is attached to an intermediate portion of the illuminating fiber 12 in a distal end portion side of the insertion portion 11.

Figure 2:
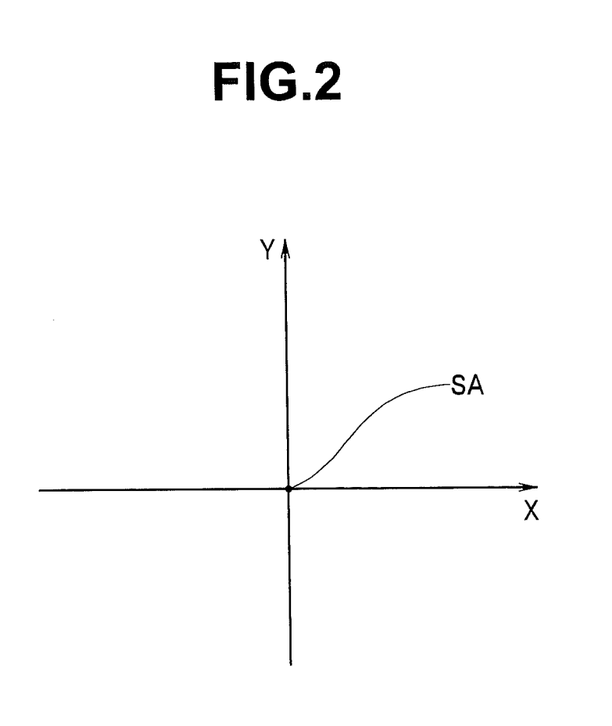
FIG. 2 is a diagram for explaining one example of a virtual XY plane that is set on a surface of an object.

Here, explanation will be made hereinafter with a case in which an XY plane as shown in FIG. 2 is set on a surface of an object as a virtual plane that is perpendicular to an insertion axis (or an optical axis of the objective optical system 14) that corresponds to an axis in a longitudinal direction of the insertion portion 11 being cited as an example. FIG. 2 is a diagram for explaining one example of the virtual XY plane that is set on the surface of an object.

More specifically a point SA on the XY plane of FIG. 2 shows an intersection point of the insertion axis and a paper surface in a case in which the insertion axis of the insertion portion 11 is assumed to be present in a direction corresponding to a direction from a front side of the paper surface to a back side and is virtually set. Further, an X axis direction in the XY plane of FIG. 2 is set as a direction toward a right side from a left side of the paper surface. Further, a Y axis direction in the XY plane of FIG. 2 is set as a direction toward an upper side from a lower side of the paper surface. Further, the X axis and the Y axis that configure the XY plane of FIG. 2 intersect each other in the point SA.

The actuator 15 is configured by having an X axis actuator (not illustrated) that acts so as to swing the end portion including the light exit face of the illuminating fiber 12 in the X axis direction based on a first drive signal that is outputted from the driver unit 22 of the main body apparatus 3, and a Y axis actuator (not illustrated) that acts to swing the end portion including the light exit face of the illuminating fiber 12 in the Y axis direction based on a second drive signal that is outputted from the driver unit 22 of the main body apparatus 3. The actuator 15 can cause the end portion including the light exit face of the illuminating fiber 12 to swing so that an irradiation position of the illuminating light with which the object is irradiated draws a locus corresponding to a predetermined scanning pattern by actions of the X axis actuator and the Y axis actuator as described above.

Inside the insertion portion 11, a memory 16 is provided, in which endoscope information including various kinds of information such as individual identification information of the scanning endoscope 2 is stored in advance. The endoscope information that is stored in the memory 16 is read by a controller 25 of the main body apparatus 3 when the scanning endoscope 2 and the main body apparatus 3 are connected.

The main body apparatus 3 is configured by having the light source unit 21, the driver unit 22, the detection unit 23, a memory 24 and the controller 25.

The light source unit 21 is configured by having a light source 31a, a light source 31b, a light source 31c and the multiplexer 32.

The light source 31a includes, for example, a laser light source, and is configured to emit a light of a wavelength band of a red color (hereinafter, also called an R light) to the multiplexer 32 when the light source 31a is turned on by control of the controller 25.

The light source 31b includes, for example, a laser light source, and is configured to emit a light of a wavelength band of a green color (hereinafter, also called a G light) to the multiplexer 32 when the light source 31b is turned on by control of the controller 25.

The light source 31c includes, for example, a laser light source, and is configured to emit a light of a wavelength band of a blue color (hereinafter, also called a B light) when the light source 31c is turned on by control of the controller 25.

The multiplexer 32 is configured to multiplex the R light emitted from the light source 31a, the G light emitted from the light source 31b, and the B light emitted from the light source 31c to be able to supply the multiplexed lights to the light incident face of the illuminating fiber 12.

The driver unit 22 is configured by having a signal generator 33, digital-analogue (hereinafter, called D/A) converters 34a and 34b, and an amplifier 35.

Figure 3:
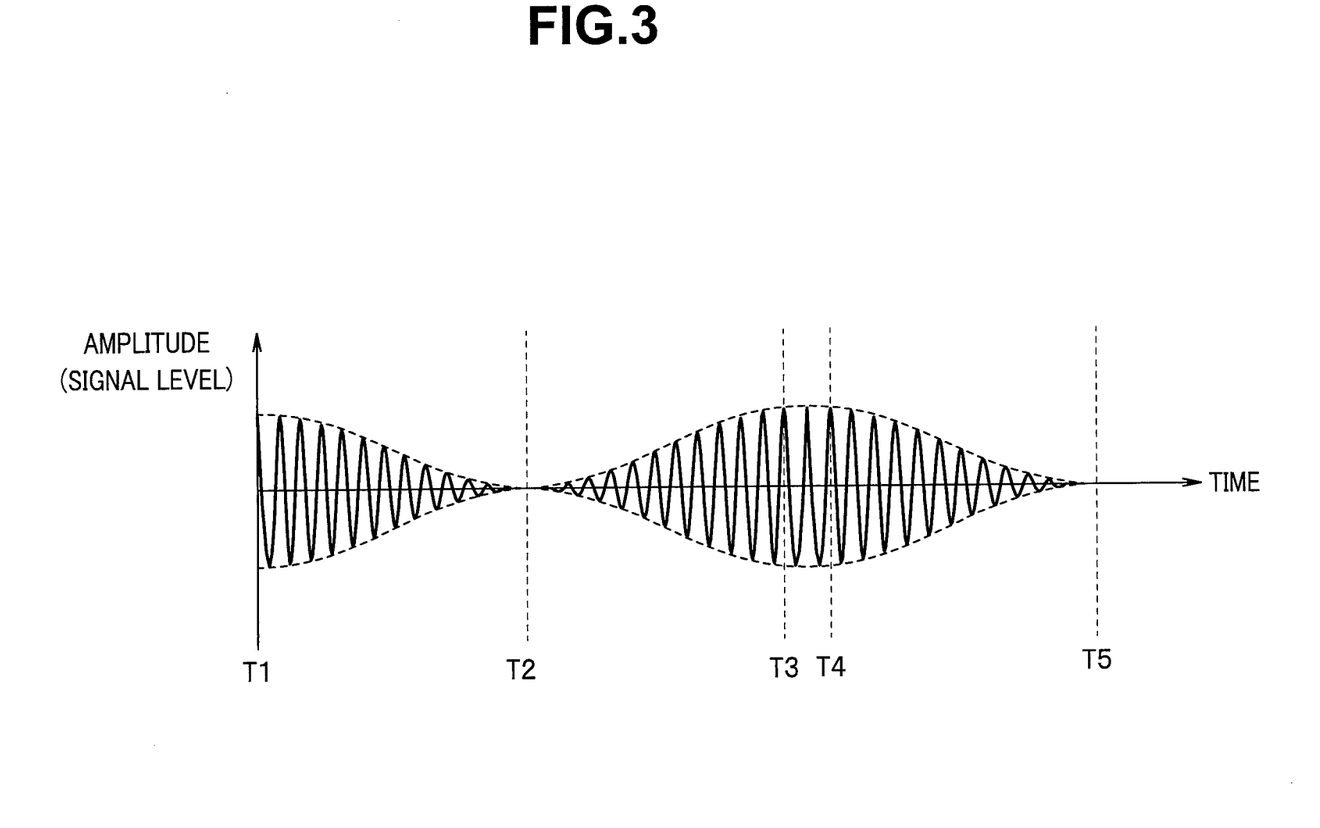
FIG. 3 is a diagram for explaining one example of a signal waveform of a drive signal that is supplied to an actuator provided in the scanning endoscope.

The signal generator 33 is configured to generate a signal of a predetermined waveform as shown in FIG. 3, for example, to output the signal to the D/A converter 34a, as the first drive signal that swings the end portion including the light exit face of the illuminating fiber 12 in the X axis direction based on control of the controller 25. FIG. 3 is a diagram for explaining one example of the signal waveform of the drive signal that is supplied to the actuator provided in the scanning endoscope.

Further, the signal generator 33 is configured to generate a signal of a waveform obtained by a phase of the aforementioned first drive signal being shifted by 90° to output the signal to the D/A converter 34b, as the second drive signal that swings the end portion including the light exit face of the illuminating fiber 12 in the Y axis direction based on control of the controller 25.

The D/A converter 34a is configured to convert the digital first drive signal outputted from the signal generator 33 into an analogue first drive signal to output the analogue first drive signal to the amplifier 35.

The D/A converter 34b is configured to convert the digital second drive signal outputted from the signal generator 33 into an analogue second drive signal to output the analogue second drive signal to the amplifier 35.

The amplifier 35 is configured to amplify the first and the second drive signals that are outputted from the D/A converters 34a and 34b to output the first and the second drive signals to the actuator 15.

Here, an amplitude value (a signal level) of the waveform of the drive signal illustrated in FIG. 3 gradually decreases with a time point T1 at which the amplitude value becomes a maximum value as a starting point, and gradually increases immediately after the amplitude value becomes zero at a time point T2 to be the maximum value at a time point T3. The amplitude value gradually decreases immediately after the amplitude value keeps the maximum value in a time period from the time point T3 to a time point T4, and becomes zero at a time point T5.

Figure 4:
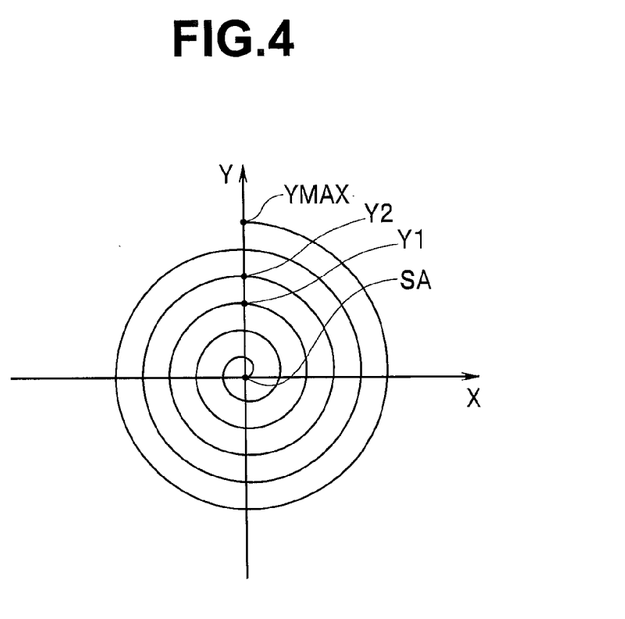
FIG. 4 is a diagram for explaining a locus in a first spiral shape that is drawn when the virtual XY plane as in FIG. 2 is scanned.
Figure 5:
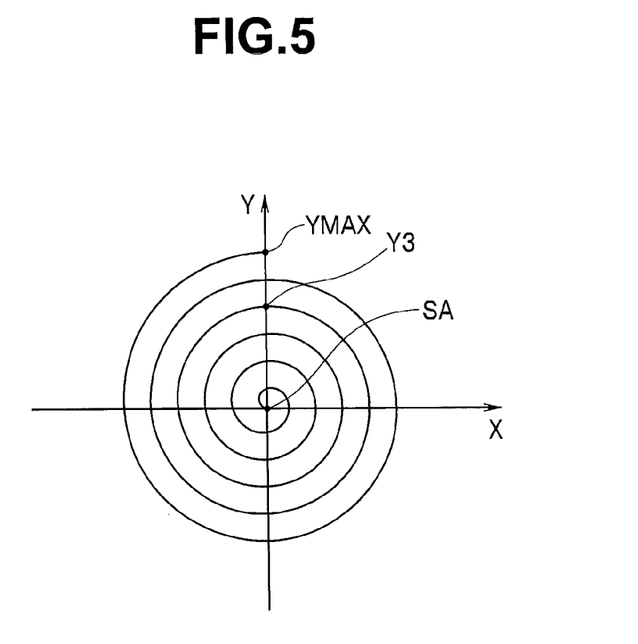
FIG. 5 is a diagram for explaining a locus in a second spiral shape that is drawn when the virtual XY plane as in FIG. 2 is scanned.
Figure 6:
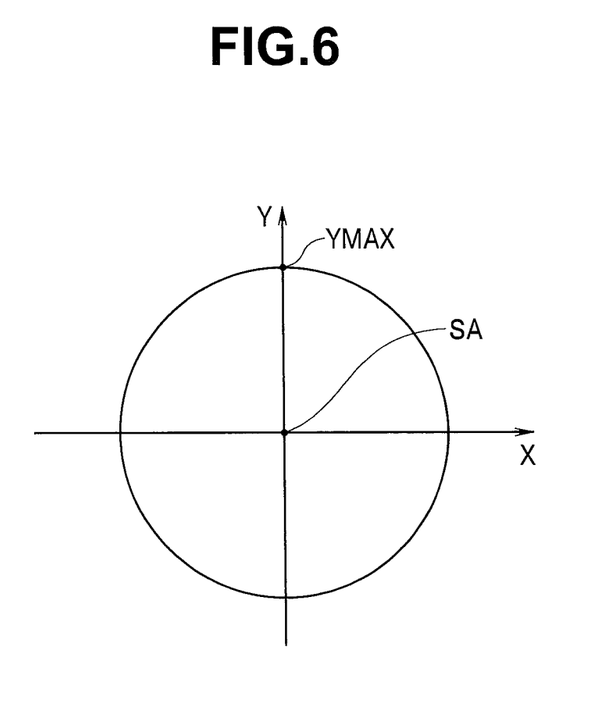
FIG. 6 is a diagram for explaining one example of a locus in a circular shape that is drawn when the virtual XY plane as in FIG. 2 is scanned.

The first drive signal including the waveform as shown in FIG. 3 is supplied to the X axis actuator of the actuator 15, and the second drive signal obtained by the phase of the first drive signal being shifted by 90° is supplied to the Y axis actuator of the actuator 15. Thereby the end portion including the light exit face of the illuminating fiber 12 is caused to swing with the point SA as a center. Further, in response to the swing of the illuminating fiber 12 as above, the locus of the illuminating light with which the surface of the object is irradiated changes in a sequence of FIG. 4 to FIG. 5 to FIG. 6 to FIG. 4 .... FIG. 4 is a diagram for explaining a locus in a first spiral shape that is drawn when the virtual XY plane as in FIG. 2 is scanned. FIG. 5 is a diagram for explaining a locus in a second spiral shape that is drawn when the virtual XY plane as in FIG. 2 is scanned. FIG. 6 is a diagram for explaining a locus in a circular shape that is drawn when the virtual XY plane as in FIG. 2 is scanned.

More specifically, in the time point T1 corresponding to a scan start timing for an object, a point YMAX that is an outermost point of irradiation coordinates of the illuminating light in the surface of the object is irradiated with the illuminating light. Subsequently, as the amplitude values of the first and the second drive signals decrease from the time point T1 to the time point T2, the irradiation coordinates of the illuminating light in the surface of the object displace in such a manner as to draw the locus in the first spiral shape inward with the point YMAX as the starting point, and further, when the time point T2 arrives, a position corresponding to a point SA in the surface of the object is irradiated with the illuminating light (see FIG. 4).

Further, as the amplitude values of the first and the second drive signals increase from the time point T2 to the time point T3, the irradiation coordinates of the illuminating light in the surface of the object displace in such a manner as to draw the locus in the second spiral shape outward with the point SA as the starting point. Further, when the time point T3 arrives, the point YMAX that is the outermost point of the irradiation coordinates of the illuminating light in the surface of the object is irradiated with the illuminating light (see FIG. 5).

Thereafter, in a time period from the time point T3 until the time point T4, the irradiation coordinates of the illuminating light in the surface of the object displace in such a manner as to circle a predetermined times along a locus in a circular shape with a radius RMAX that corresponds to a distance between the point SA and the point YMAX (see FIG. 6).

Subsequently, as the amplitude values of the first and the second drive signals decrease from the time point T4 to the time point T5, the irradiation coordinates of the illuminating light in the surface of the object displace in such a manner as to draw the locus in the first spiral shape inward with the point YMAX as the starting point. Further, when the time point T5 arrives, the point SA in the surface of the object is irradiated with the illuminating light (see FIG. 4).

The detection unit 23 is configured by having the demultiplexer 36, detectors 37a, 37b and 37c, and analogue-digital (hereinafter, called A/D) converters 38a, 38b and 38c.

The demultiplexer 36 includes a dichroic mirror or the like, and is configured to separate the return light emitted from the light exit face of the light receiving fiber 13 into lights of respective color components of R (red), G (green) and B (blue) to emit the lights to the detectors 37a, 37b and 37c.

The detector 37a is configured to detect intensity of the R light that is outputted from the demultiplexer 36, generate an analogue R signal corresponding to the detected intensity of the R light and output the analogue R signal to the A/D converter 38a.

The detector 37b is configured to detect intensity of the G light that is outputted from the demultiplexer 36, generate an analogue G signal corresponding to the detected intensity of the G light and output the analogue G signal to the A/D converter 38b.

The detector 37c is configured to detect intensity of the B light that is outputted from the demultiplexer 36, generate an analogue B signal corresponding to the detected intensity of the B light and output the analogue B signal to the A/D converter 38c.

The A/D converter 38a is configured to convert the analogue R signal that is outputted from the detector 37a into a digital R signal and output the digital R signal to the controller 25.

The A/D converter 38b is configured to convert the analogue G signal that is outputted from the detector 37b into a digital G signal and output the digital G signal to the controller 25.

The A/D converter 38c is configured to convert the analogue B signal that is outputted from the detector 37c into a digital B signal and output the digital B signal to the controller 25.

In the memory 24, a control program for performing control of the main body apparatus 3 and the like are stored in advance. Further, in the memory 24, the endoscope information that is read by the controller 25 of the main body apparatus 3 is stored.

The controller 25 includes a CPU or the like, and is configured to read the control program stored in the memory 24, and perform control of the light source unit 21 and the driver unit 22 based on the control program that is read.

The controller 25 is configured to be able to generate an image based on the respective color signals that are outputted from the detection unit 23 and cause the monitor 4 to display the image, while the controller 25 keeps control for supplying the illuminating light to the illuminating fiber 12 from the light source unit 21, and control for supplying the drive signal to the actuator 15 from the driver unit 22, respectively.

More specifically, the controller 25 generates an image corresponding to one frame based on the respective color signals outputted from the detection unit 23 in the time period corresponding to the time period from the time point T1 to the time point T2, and an image corresponding to one frame based on the respective color signals outputted from the detection unit 23 in the time period corresponding to the time period from the time point T2 to the time point T3, during the time period from the time point T3 until the time point T4 and causes the monitor 4 to display the images, while the controller 25 keeps control for supplying the illuminating light to the illuminating fiber 12 from the light source unit 21, and control for supplying the drive signal to the actuator 15 from the driver unit 22 respectively. Namely, the respective color signals that are outputted from the detection unit 23 during the time period corresponding to the time period from the time point T3 to the time point T4 do not contribute to generation of the images.

According to the embodiment described above, an action similar to the action in the time period from the time point T3 to the time point T4 described above is performed every fixed time period in which scanning for obtaining the image corresponding to two frames is completed. Therefore, according to the embodiment described above, a timing relating to irradiation of the illuminating light to the object, and a timing relating to generation of the image corresponding to the return light from the object can be favorably synchronized without control or the like that temporarily stops at least any one of swing of the illuminating fiber 12 and supply of the illuminating light to the illuminating fiber 12 being performed. As a result, according to the embodiment described above, stability of a frame rate at a time of observation using the scanning endoscope can be enhanced as compared with the conventional system.

Figure 7:
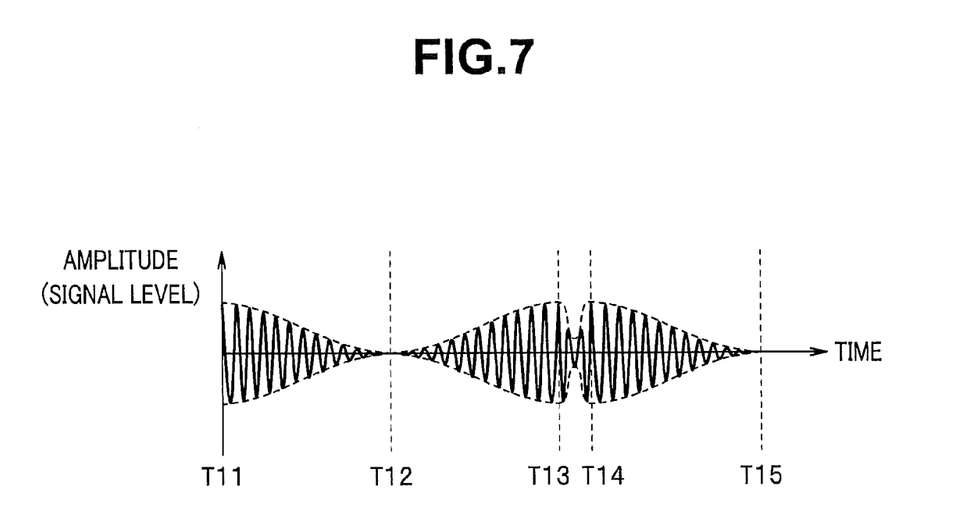
FIG. 7 is a diagram for explaining a first modification of a signal waveform of a drive signal that is supplied to the actuator provided in the scanning endoscope.

Note that according to the present embodiment, instead of the drive signal that includes the waveform illustrated in FIG. 3, a drive signal including a waveform as shown in FIG. 7, for example, may be supplied to the actuator 15. FIG. 7 is a diagram for explaining a first modification of the signal waveform of the drive signal that is supplied to the actuator provided in the scanning endoscope.

Here, an amplitude value (a signal level) of the waveform of the drive signal illustrated in FIG. 7 gradually decreases with a time point T11 at which the amplitude value becomes a maximum value as a starting point, and gradually increases immediately after the amplitude value becomes zero at a time point T12 to be the maximum value at a time point T13. The amplitude value is attenuated to a predetermined value that is less than the maximum value during the time period from a time substantially immediately after the time point T13 to a time substantially immediately before a time point T14, is amplified to the maximum value at the time point T14 again, and gradually decreases from a time immediately after the time point T14 to be zero at a time point T15. Note that the aforementioned predetermined value may be properly set in accordance with, for example, a length of the end portion of the illuminating fiber 12 that is caused to swing by the actuator 15, or the like.

Figure 8:
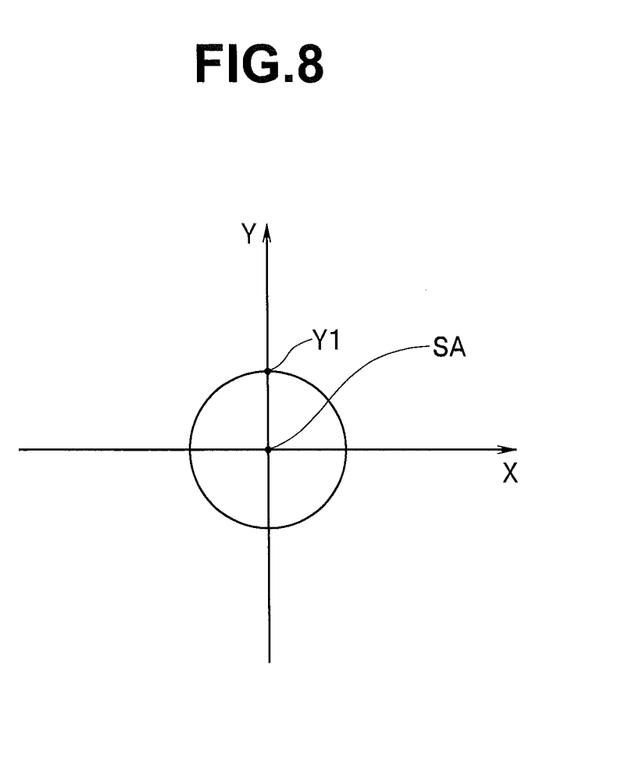
FIG. 8 is a diagram for explaining an example, which differs from FIG. 6, of the locus in the circular shape that is drawn when the virtual XY plane as in FIG. 2 is scanned.

The first drive signal including the waveform as shown in FIG. 7 is supplied to the X axis actuator of the actuator 15, and the second drive signal that is obtained by the phase of the first drive signal being shifted by 90° is supplied to the Y axis actuator of the actuator 15, whereby the end portion including the light exit surface of the illuminating fiber 12 is caused to swing with the point SA as the center. Further, in response to the swing of the illuminating fiber 12 as above, the locus of the illuminating light with which the surface of the object is irradiated changes in a sequence of FIG. 4 to FIG. 5 to FIG. 8 to FIG. 4 . . . . FIG. 8 is a diagram for explaining an example, which differs from FIG. 6, of the locus in the circular shape that is drawn when the virtual XY plane as in FIG. 2 is scanned.

More specifically, at the time point T11 corresponding to the scan start timing for an object, the point YMAX that is the outermost point of the irradiation coordinates of the illuminating light in the surface of the object is irradiated with the illuminating light. Subsequently, as the amplitude values of the first and the second drive signals decrease from the time point T11 to the time point T12, the irradiation coordinates of the illuminating light in the surface of the object displace in such a manner as to draw the locus in the first spiral shape inward with the point YMAX as the starting point. Further, when the time point T12 arrives, the position corresponding to the point SA on the surface of the object is irradiated with the illuminating light (see FIG. 4).

Further, as the amplitude values of the first and the second drive signals increase from the time point T12 to the time point T13, the irradiation coordinates of the illuminating light in the surface of the object displace in such a manner as to draw the locus in the second spiral shape outward with the point SA as the starting point. Further, when the time point T13 arrives, the point YMAX that is the outermost point of the irradiation coordinates of the illuminating light in the surface of the object is irradiated with the illuminating light (see FIG. 5).

Thereafter, in the time period from the time substantially immediately after the time point T13 to the time substantially immediately before the time point T14, the irradiation coordinates of the illuminating light in the surface of the object displace so as to circle predetermined times along a locus in a circular shape with a radius R1 (<RMAX) that corresponds to a distance between the point SA and a point Y1 (see FIG. 8).

Subsequently, as the amplitude values of the first and the second drive signals decrease from the time point T14 to the time point T15, the irradiation coordinates of the illuminating light in the surface of the object displace in such a manner as to draw the locus in the first spiral shape inward with the point YMAX as the starting point. Further, when the time point T15 arrives, the point SA in the surface of the object is irradiated with the illuminating light (see FIG. 4).

The controller 25 generates an image corresponding to one frame based on the respective color signals that are outputted from the detection unit 23 in a time period corresponding to a time period from the time point T11 to the time point T12, and an image corresponding to one frame based on the respective color signals that are outputted from the detection unit 23 in a time period corresponding to a time period from the time point T12 to the time point T13, during a time period from the time point T13 until the time point T14 and causes the monitor 4 to display the images, while the controller 25 keeps control for supplying the illuminating light to the illuminating fiber 12 from the light source unit 21, and control for supplying the drive signal to the actuator 15 from the driver unit 22 respectively. Namely, the respective color signals that are outputted from the detection unit 23 during the time period corresponding to the time period from the time point T13 to the time period T14 do not contribute to generation of the images.

According to the first modification described above, an action similar to the action in the time period from the time point T13 to the time point T14 described above is performed every fixed time period in which scanning for obtaining the image corresponding to two frames is completed. Therefore, according to the first modification described above, a timing relating to irradiation of the illuminating light to the object, and a timing relating to generation of the image corresponding to the return light from the object can be favorably synchronized, without control or the like that temporarily stops at least any one of swing of the illuminating fiber 12 and supply of the illuminating light to the illuminating fiber 12 being performed. As a result, according to the first modification described above, stability of the frame rate at the time of observation with use of the scanning endoscope can be enhanced as compared with the conventional system.

Figure 9:
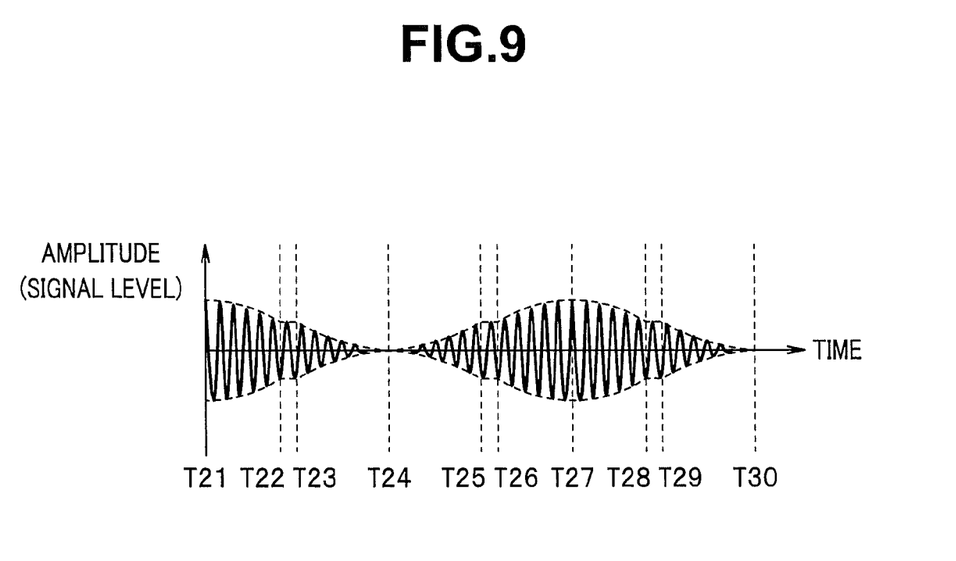
FIG. 9 is a diagram for explaining a second modification of the signal waveform of the drive signal that is supplied to the actuator provided in the scanning endoscope.

Note that according to the present embodiment, instead of the drive signal including the waveform illustrated in FIG. 3 or FIG. 7, a drive signal including a waveform as shown in FIG. 9, for example, may be supplied to the actuator 15. FIG. 9 is a diagram for explaining a second modification of the signal waveform of the drive signal that is supplied to the actuator provided in the scanning endoscope.

Here, an amplitude value (a signal level) of the waveform of the drive signal illustrated in FIG. 9 gradually decreases until a time point T22 with a time point T21 at which the amplitude value becomes a maximum value as a starting point, keeps a predetermined value in a time period from the time point T22 until a time point T23, and gradually decreases from the time point T23 to be zero at a time point T24. The amplitude value gradually increases from a time immediately after the amplitude value becomes zero at the time point T24 until a time point T25, keeps a predetermined value in a time period from the time point T25 to a time point T26, and gradually increases from the time point T26 to be a maximum value at a time point T27. The amplitude value gradually decreases from the time point 27 until a time point T28, keeps a predetermined value in a time period from the time point T28 to a time point T29, and gradually decreases from the time point T29 to be zero at a time point T30.

Figure 10:
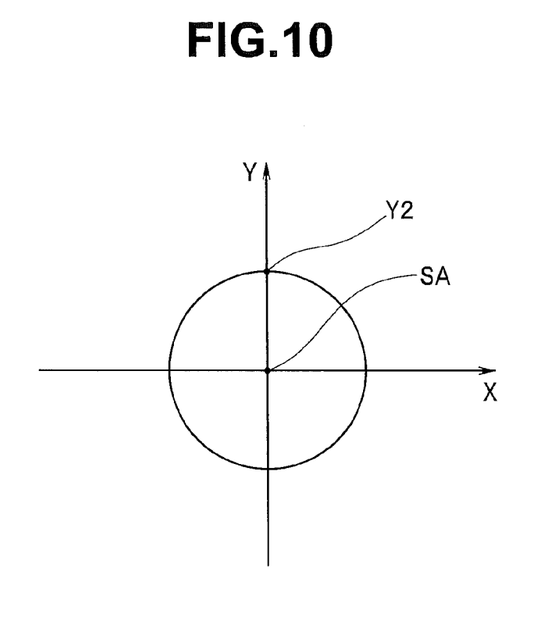
FIG. 10 is a diagram for explaining an example, which differs from FIG. 6 and FIG. 8, of the locus in the circular shape that is drawn when the virtual XY plane as in FIG. 2 is scanned.
Figure 11:
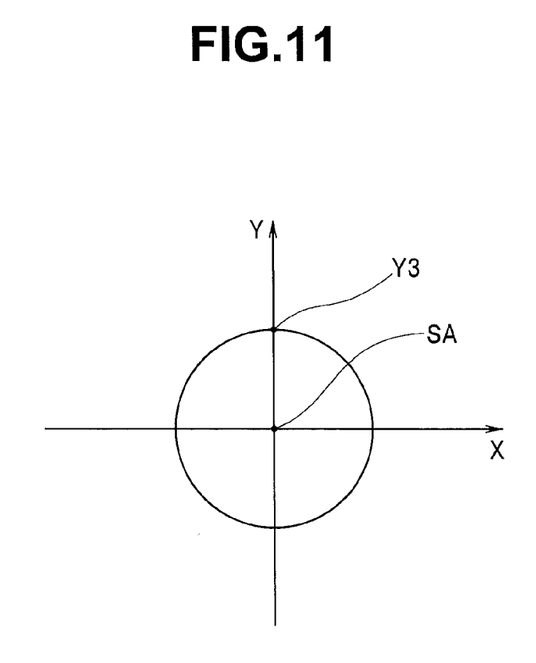
FIG. 11 is a diagram for explaining an example, which differs from FIG. 6, FIG. 8 and FIG. 10, of the locus in the circular shape that is drawn when the virtual XY plane as in FIG. 2 is scanned.

A first drive signal including the waveform as shown in FIG. 9 is supplied to the X axis actuator of the actuator 15, and a second drive signal obtained by a phase of the first drive signal being shifted by 90° is supplied to the Y axis actuator of the actuator 15. Thereby, the end portion including the light exit face of the illuminating fiber 12 is caused to swing with the point SA as a center. Further, in response to the swing of the illuminating fiber 12 as above, the irradiation position of the illuminating light that is irradiated along the locus in the spiral shape of FIG. 4 temporarily shifts to a locus in a circular shape illustrated in FIG. 10, and the irradiation position of the illuminating light that is irradiated along the locus in the spiral shape of FIG. 5 temporarily shifts to a locus in a circular shape illustrated in FIG. 11. FIG. 10 is a diagram for explaining an example, which differs from FIG. 6 and FIG. 8, of the locus in the circular shape that is drawn when the virtual XY plane as in FIG. 2 is scanned. FIG. 11 is a diagram for explaining an example, which differs from FIG. 6, FIG. 8 and FIG. 10, of the locus in the circular shape that is drawn when the virtual XY plane as in FIG. 2 is scanned.

More specifically, at the time point T21 corresponding to a scan start timing for an object, the point YMAX that is the outermost point of the irradiation coordinates of the illuminating light in the surface of the object is irradiated with the illuminating light. Subsequently, as the amplitude values of the first and the second drive signals decrease from the time point T21 to the time point T22, the irradiation coordinates of the illuminating light in the surface of the object displace in such a manner as to draw the locus in the first spiral shape inward with the point YMAX as the starting point. Further, when the time point T22 arrives, a position corresponding to a point Y2 in the surface of the object is irradiated with the illuminating light (see FIG. 4).

In the time period from the time point T22 until the time point T23, the irradiation coordinates of the illuminating light in the surface of the object displace so as to circle predetermined times along a locus in a circular shape with a radius R2 (<RMAX) that corresponds to a distance between the point SA and the point Y2 (see FIG. 10).

Thereafter, as the amplitude values of the first and the second drive signals decrease from the time point T23 to the time point T24, the irradiation coordinates of the illuminating light in the surface of the object displace in such a manner as to draw the locus in the first spiral shape inward with the point Y2 as the starting point. Further, when the time point T24 arrives, the position corresponding to the point SA in the surface of the object is irradiated with the illuminating light (see FIG. 4).

Further, as the amplitude values of the first and the second drive signals increase from the time period T24 to the time period T25, the irradiation coordinates of the illuminating light in the surface of the object displace in such a manner as to draw the locus in the second spiral shape outward with the point SA as the starting point. Further, when the time point T25 arrives, a position corresponding to a point Y3 in the surface of the object is irradiated with the illuminating light (see FIG. 5).

In the time period from the time point T25 until the time point T26, the irradiation coordinates of the illuminating light in the surface of the object displace so as to circle predetermined times along a locus in a circular shape with a radius R3 (<RMAX) that corresponds to a distance between the point SA and the point Y3 (see FIG. 11).

Thereafter, as the amplitude values of the first and the second drive signals increase from the time point T26 to the time point T27, the irradiation coordinates of the illuminating light in the surface of the object displace in such a manner as to draw the locus in the second spiral shape outward with the point Y3 as the starting point. Further, when the time point T27 arrives, the position corresponding to the point YMAX in the surface of the object is irradiated with the illuminating light (see FIG. 5).

Subsequently, as the amplitude values of the first and the second drive signals decrease from the time point T27 to the time point T28, the irradiation coordinates of the illuminating light in the surface of the object displace in such a manner as to draw the locus in the first spiral shape inward with the point YMAX as the starting point. Further, when the time point T28 arrives, the position corresponding to the point Y2 in the surface of the object is irradiated with the illuminating light (see FIG. 4).

In the time period from the time point T28 until the time point T29, the irradiation coordinates of the illuminating light in the surface of the object displace so as to circle a predetermined times along the locus in the circular shape with the radius R2 (<RMAX) that corresponds to the distance between the point SA and the point Y2 (see FIG. 10).

Thereafter, as the amplitude values of the first and the second drive signals decrease from the time point T29 to the time point T30, the irradiation coordinates of the illuminating light in the surface of the object displace in such a manner as to draw the locus in the first spiral shape inward with the point Y2 as the starting point. Further, when the time point T30 arrives, the position corresponding to the point SA in the surface of the object is irradiated with the illuminating light (see FIG. 4).

The controller 25 generates an image of a first half portion based on the respective color signals, which are outputted from the detection unit 23 in a time period corresponding to a time period from the time point T21 to the time point T22, during a time period from the time point T22 until the time point T23, generates an image of a latter half portion based on the respective color signals, which are outputted from the detection unit 23 in a time period corresponding to a time period from the time point T23 to the time point T24, during a time period from the time point T25 until the time point T26, and further generates an image corresponding to one frame obtained by the image of the first half portion and the image of the latter half portion being synthesized during the time period from the time point T25 until the time point T26 to cause the monitor 4 to display the image corresponding to one frame, while the controller 25 keeps control for supplying the illuminating light to the illuminating fiber 12 from the light source unit 21, and control for supplying the drive signal to the actuator 15 from the driver unit 22 respectively. Namely, the respective color signals that are outputted from the detection unit 23 during the time period corresponding to the time period from the time point T22 to the time point T23, and during the time period from the time point T25 until the time point T26 do not contribute to generation of the image.

Further, the controller 25 generates an image of a first half portion based on the respective color signals, which are outputted from the detection unit 23 in a time period corresponding to a time period from the time point T24 to the time point T25, during a time period from the time point T25 until the time point T26, generates an image of a latter half portion based on the respective color signals, which are outputted from the detection unit 23 in a time period corresponding to a time period from the time point T26 to the time point T27, during a time period from the time point T28 until the time point T29, and further generates an image corresponding to one frame obtained by the image of the first half portion and the image of the latter half portion being synthesized during the time period from the time T28 until the time T29 to cause the monitor 4 to display the image corresponding to one frame, while the controller 25 keeps control for supplying the illuminating light to the illuminating fiber 12 from the light source unit 21, and control for supplying the drive signal to the actuator 15 from the driver unit 22 respectively. Namely, the respective color signals that are outputted from the detection unit 23 during the time period corresponding to the time period from the time point T28 to the time point T29 do not contribute to generation of the image.

According to the second modification described above, an action similar to any one of the action in the time period from the time point T22 to the time point T23, the action in the time period from the time point T25 to the time period T26, and the action in the time period from the time point T28 to the time point T29 is performed every predetermined time period provided in the process of scanning for obtaining the image corresponding to one frame. Therefore, according to the second modification described above, the timing relating to irradiation of the illuminating light to the object, and the timing relating to generation of the image corresponding to the return light from the object can be favorably synchronized without control or the like that temporarily stops at least any one of swing of the illuminating fiber 12 and supply of the illuminating light to the illuminating fiber 12 being performed. As a result, according to the second modification described above, stability of the frame rate at the time of observation with use of the scanning endoscope can be enhanced as compared with the conventional system.

Figure 12:
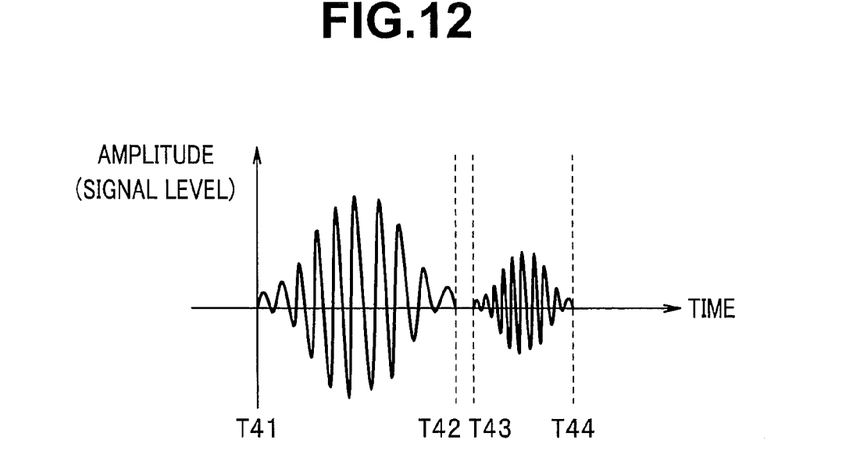
FIG. 12 is a diagram for explaining a third modification of the signal waveform of the drive signal that is supplied to the actuator that is provided in the scanning endoscope.

Note that according to the present embodiment, instead of the drive signal including the waveform illustrated in FIG. 3, FIG. 7 or FIG. 9, a drive signal including a waveform as shown in FIG. 12, for example, may be supplied to the actuator 15. FIG. 12 is a diagram for explaining a third modification of the signal waveform of the drive signal that is supplied to the actuator provided in the scanning endoscope.

Here, a first drive signal including the waveform as shown in FIG. 12 is supplied to the X axis actuator of the actuator 15, and a second drive signal that is obtained by a phase of the first drive signal being shifted by 90° is supplied to the Y axis actuator of the actuator 15. Thereby, in each of a time period from a time point T41 until a time point T42, and a time period from a time point T43 until a time point T44, the end portion including the light exit face of the illuminating fiber 12 is caused to swing in such a manner as to draw a locus in a spiral shape with the point SA as a center, namely, in a sequence of the locus in the second spiral shape as illustrated in FIG. 5 to the locus in the first spiral shape as illustrated in FIG. 4.

Note that according to the waveform of the drive signal shown in FIG. 12, a maximum amplitude value in the time period from the time point T43 until the time point T44 is set to be smaller as compared with a maximum amplitude value in the time period from the time point T41 until the time point T42. Therefore, according to the waveform of the drive signal shown in FIG. 12, when a coordinate position of an outermost point of the irradiation coordinates of the illuminating light in the time period from the time point T41 until the time point T42 is set as a point YMAX1, and a coordinate position of an outermost point of the irradiation coordinates of the illuminating light in the time period from the time point T43 until the time point T44 is set as a point YMAX2, for example, the relation of YMAX1>YMAX2 is established.

The controller 25 generates an image corresponding to two frames based on the respective color signals, which are outputted from the detection unit 23 in the time period corresponding to the time period from the time point T41 to the time point T42, during the time period from the time point T43 until the time point T44 to cause the monitor 4 to display the image, while the controller 25 keeps control for supplying the illuminating light to the illuminating fiber 12 from the light source unit 21, and control for supplying the drive signal to the actuator 15 from the driver unit 22. Namely, the respective color signals that are outputted from the detection unit 23 during the time period corresponding to the time period from the time point T43 to the time period T44 do not contribute to generation of the image.

According to the third modification described above, an action similar to the action in the time period from the time point T43 to the time point T44 that is described above is performed every fixed time period in which scanning for obtaining the image corresponding to two frames is completed. Therefore, according to the third modification described above, the timing relating to irradiation of the illuminating light to the object, and the timing relating to generation of the image corresponding to the return light from the object can be favorably synchronized, without control or the like that temporarily stops at least any one of swing of the illuminating fiber 12 and supply of the illuminating light to the illuminating fiber 12 being performed. As a result, according to the third modification described above, stability of the frame rate at the time of observation with use of the scanning endoscope can be enhanced as compared with the conventional system.

Figure 13:
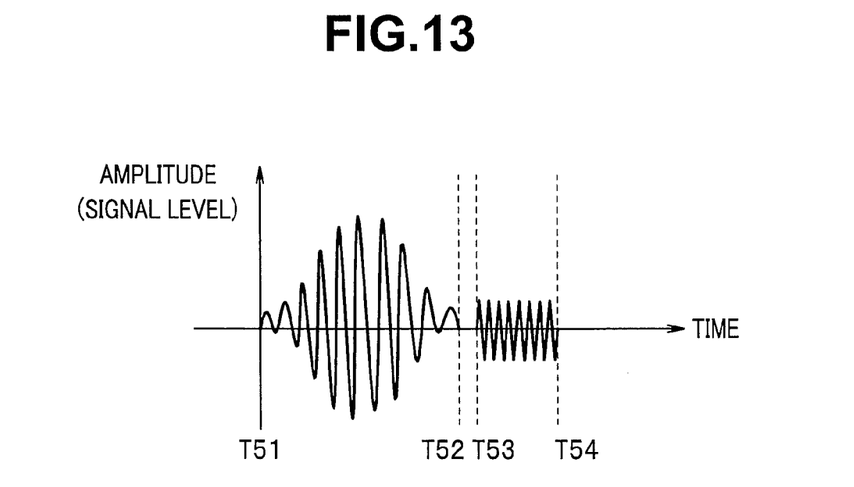
FIG. 13 is a diagram for explaining a fourth modification of the signal waveform of the drive signal that is supplied to the actuator that is provided in the scanning endoscope.

Note that according to the present embodiment, instead of the drive signal including the waveform illustrated in FIG. 3, FIG. 7, FIG. 9 or FIG. 12, a drive signal including a waveform as shown in FIG. 13, for example, may be supplied to the actuator 15. FIG. 13 is a diagram for explaining a fourth modification of the signal waveform of the drive signal that is supplied to the actuator provided in the scanning endoscope.

Here, a first drive signal including the waveform as shown in FIG. 13 is supplied to the X axis actuator of the actuator 15, and a second drive signal that is obtained by a phase of the first drive signal being shifted by 90° is supplied to the Y axis actuator of the actuator 15. Thereby, in a time period from a time point T51 until a time point T52, the end portion including the light exit face of the illuminating fiber 12 is caused to swing in such a manner as to draw a locus in a spiral shape with the point SA as a center, namely, in a sequence of the locus in the second spiral shape as illustrated in FIG. 5 to the locus in the first spiral shape as illustrated in FIG. 4.

Further, the first drive signal including the waveform as shown in FIG. 13 is supplied to the X axis actuator of the actuator 15, and the second drive signal obtained by the phase of the first drive signal being shifted by 90° is supplied to the Y axis actuator of the actuator 15. Thereby, in a time period from a time point T53 until a time point T54, the end portion including the light exit face of the illuminating fiber 12 is caused to swing in such a manner as to draw a locus in a circular shape with the point SA as the center.

Note that according to the waveform of the drive signal shown in FIG. 13, a maximum amplitude value (a signal level) in the time period from the time point T53 until the time point T54 is set to include a fixed value that is larger than zero and smaller as compared with a maximum amplitude value in the time period from the time point T51 until the time point T52. Therefore, according to the waveform of the drive signal shown in FIG. 13, in the time period from the time point T53 until the time point T54, the end portion including the light exit face of the illuminating fiber 12 may be caused to swing along the locus in the circular shape of FIG. 8, may be caused to swing along the locus in the circular shape of FIG. 10, or may be caused to swing along the locus in the circular shape of FIG. 11, for example.

The controller 25 generates an image corresponding to two frames based on the respective color signals, which are outputted from the detection unit 23 in the time period corresponding to the time period from the time point T51 to the time point T52, during the time period from the time point T53 until the time point T54 to cause the monitor 4 to display the image, while the controller 25 keeps control for supplying the illuminating light to the illuminating fiber 12 from the light source unit 21, and control for supplying the drive signal to the actuator 15 from the driver unit 22, respectively. Namely, the respective color signals that are outputted from the detection unit 23 during the time period corresponding to the time period from the time point T53 to the time point T54 do not contribute to generation of the image.

According to the fourth modification described above, an action similar to the action in the time period from the time point T53 to the time point T54 that is described above is performed every fixed time period in which scanning for obtaining the image corresponding to two frames is completed. Therefore, according to the fourth modification described above, the timing relating to irradiation of the illuminating light to the object, and the timing relating to generation of the image corresponding to the return light from the object can be favorably synchronized without control or the like that temporarily stops at least any one of swing of the illuminating fiber 12 and supply of the illuminating light to the illuminating fiber 12 being performed. As a result, according to the fourth modification described above, stability of the frame rate at the time of observation with use of the scanning endoscope can be enhanced as compared with the conventional system.

The present invention is not limited to the embodiment and the modifications described above, and various changes and applications can be made within the range without departing from the gist of the invention, as a matter of course.

What is claimed is:

1. A scanning endoscope system, comprising:
    a fiber that guides an illuminating light emitted from a light source and emits the guided light to an object from a distal end of the fiber;
    an actuator capable of performing:
        a spiral scan causing the fiber to swing for scanning the object by displacing an irradiation position of the illuminating light in a spiral shape such that a distance between the irradiation position of the illuminating light and a predetermined position of the object gradually changes with the predetermined position at the center, and
        a circular scan causing the fiber to swing for scanning the object by displacing the irradiation position of the illuminating light in a circular shape such that a distance between the irradiation position of the illuminating light and the predetermined position is constant with the predetermined position of the object at the center;
    a detector that is configured to receive a return light of the illuminating light that is irradiated to the object, generate a signal corresponding to intensity of the return light, and output the signal;
    an image generating portion that generates an image of the object on the basis of a signal corresponding to an intensity of return light from the object subjected to the spiral scan by the actuator; and
    a controller configured to control the actuator to perform the circular scan in a time period in which the image generating portion is generating an image of the object, and control the actuator to perform the spiral scan in a time period other than the time period in which the image generating portion is generating the image of the object.

2. The scanning endoscope system according to claim 1, wherein the controller sequentially performs a first spiral scan in which the object is scanned by spirally displacing the irradiation position of the illuminating light toward a center point from an outermost point, and a second spiral scan in which the object is scanned by spirally displacing the irradiation position of the illuminating light toward the outermost point from the center point, and
    the image generating portion generates an image of the object on the basis of a signal corresponding to an intensity of return light from the object subjected to at least one of the first spiral scan and the second spiral scan in a time period other than the time period in which the first spiral scan and the second spiral scan are performed by the controller.

3. The scanning endoscope system according to claim 2, wherein the controller performs control for driving the actuator to perform the first spiral scan, the second spiral scan and the circular scan in this order.

4. The scanning endoscope system according to claim 2, wherein the controller performs control for driving the actuator so that a radius in the circular scan is not larger than a distance between the center point and the outermost point.

5. The scanning endoscope system according to claim 2, wherein the controller performs control for driving the actuator so as to shift to the circular scan temporarily in the middle of the first spiral scan, and shift to the circular scan temporarily in the middle of the second spiral scan.

6. The scanning endoscope system according to claim 2, wherein the image generating portion generates the first image in a first image generating period which is set as a time period in which the circular scan is performed by being shifted from the second spiral scan, and generates the second image in a second image generating period which is set as a time period in which the circular scan is performed by being shifted from the first spiral scan.

7. The scanning endoscope system according to claim 1, wherein the image generating portion generates an image of the object on the basis of a signal corresponding to an intensity of return light from the object subjected to the spiral scan without using a signal corresponding to an intensity of return light of the object subjected to the circular scan.

* * * * *